US00PP11951P2

(12) United States Plant Patent
Parsons

(10) Patent No.: US PP11,951 P2
(45) Date of Patent: Jun. 19, 2001

(54) VERBENA PLANT NAMED 'BALWILDAAV'

(75) Inventor: Carolyn T. Parsons, San Antonio, TX (US)

(73) Assignee: Ball Floraplant, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 09/475,965

(22) Filed: Dec. 31, 1999

(51) Int. Cl.[7] ..... A01D 5/00
(52) U.S. Cl. ..... Plt./308
(58) Field of Search ..... Plt./308

*Primary Examiner*—Bruce R. Campell
*Assistant Examiner*—Annette H. Para
(74) *Attorney, Agent, or Firm*—C. A. Whealy

(57) ABSTRACT

A new and distinct cultivar of Verbena plant named 'Balwildaav', characterized by its purple-colored flowers; mounded, low-growing, decumbent plant habit; and freely basal-branching.

1 Drawing Sheet

BACKGROUND OF THE INVENTION

The present invention relates to a new and distinct cultivar of Verbena plant, botanically known as *Verbena×hybrida,* and hereinafter referred to by the cultivar name Balwildaav.

The new Verbena is a product of a planned breeding program conducted by the Inventor in Somerville, Tenn. The objective of the breeding program was to develop new cultivars with a mounded decumbent plant habit, continuous flowering, freely-branching growth habit, and attractive flower and foliage colors.

The new Verbena originated from self-pollination made by the Inventor of the *Verbena×hybrida* cultivar Blue Princess, not patented. The cultivar Balwildaav was discovered and selected by the Inventor as a flowering plant within the progeny of the stated cross in a controlled environment in Somerville in 1997. Plants of the new Verbena differs from plants of the cultivar Blue Princess and a sibling cultivar, Balwilblu (U.S. Plant Patent application filed concurrently with this application) primarily in flower color.

Asexual reproduction of the new cultivar by terminal cuttings taken at Somerville has shown that the unique features of this new Verbena are stable and reproduced true to type in successive generations of asexual reproduction.

SUMMARY OF THE INVENTION

The following traits have been repeatedly observed and are determined to be the unique characteristics of 'Balwildaav'. These characteristics in combination distinguish 'Balwildaav' as a new and distinct cultivar:

1. Purple-colored flowers.
2. Mounded, low-growing, decumbent plant habit.
3. Freely basal-branching.

The new Verbena can be compared to the cultivar, Sunmaref TP-V, disclosed in U.S. Plant Pat. No. 9,411. However, in side-by-side comparisons conducted by the Inventor in Somerville plants of the new Verbena differ from plants of the cultivar Sunmaref TP-V in the following characteristics:

1. Plants of the new Verbena have larger flowers than plants of the cultivar Sunmarek TP-V.
2. Plants of the new Verbena have fewer flowers per spike than plants of the cultivar Sunmarek TP-V.

3. Plants of the new Verbena and the cultivar Sunmaref TP-V differ in flower color.

BRIEF DESCRIPTION OF THE PHOTOGRAPH

The accompanying photograph illustrates the overall appearance of the new cultivar as true as it reasonably possible to obtain in colored reproductions of this type. Colors in the photographs may differ slightly from the color values cited in the detailed botanical description which more accurately describe the actual colors of the new Verbena. The photograph comprises a top perspective view of typical flowers of 'Balwildaav'.

DETAILED BOTANICAL DESCRIPTION

The cultivar Balwildaav has not been observed under all possible environmental conditions. The phenotype may vary somewhat with variations in environment such as temperature and light intensity, without, however, any variance in genotype. The following observations and measurements describe plants about 10 weeks after planting rooted cuttings and grown 10-cm pots in West Chicago, Ill., under commercial practice in a double-layered acrylic-covered greenhouse with day temperatures about 21° C., night temperatures about 19° C., and light levels about 2,500 to 3,500 footcandles.

In the following description, color references are made to The Royal Horticultural Society Colour Chart except where general terms of ordinary dictionary significance are used.

Botanical classification: *Verbena×hybrida* cultivar Balwildaav.

Parentage: Self-pollination of *Verbena×hybrida* cultivar Blue Princess, not patented.

Propagation:

*Type cutting.*—Terminal cuttings.
*Time to initiate roots.*—About 7 days with 18° C.
*Time to develop roots.*—About 21 days with 18° C.
*Root description.*—Fibrous, fine, freely branching.

Plant description:

*Plant form.*—Mounded, low-growing, decumbent.
*Growth and branching habit.*—Very vigorous. Freely basal-branching, dense and bushy growth. Appropriate for 10-cm and larger containers.

*Crop time.*—About 4 to 6 weeks are required to produce a finished flowering plant from a rooted cutting in a 10-cm container.

*Plant height.*—About 6 cm.

*Plant width.*—About 35 cm.

*Lateral branches.*—Diameter: About 2 mm. Internode length: About 4.3 cm. Texture: Scabrous. Color: 144A.

*Foliage description.*—Leaves simple; generally symmetrical, abundant, opposite. Length: About 5.9 cm. Width: About 2.5 cm. Shape: Oblanceolate. Base: Attenuate. Margin: Serrate. Texture: Upper, scabrous; lower, scabrous along veins. Color: Fully expanded leaves, upper surface: Close to 137A. Fully expanded leaves, lower surface: Close to 137C. Venation, both surfaces: Close to 146D. Petiole: Length: About 2 mm. Diameter: About 2 mm. Color: 145B.

Flower description:

*Flower type and habit.*—Purple-colored salverform flowers arranged on terminal spikes. Five-lobed corolla. Freely and continuously flowering. Usually about 23 flowers per spike. Flowers typically face upright. Flowers not fragrant.

*Flowering season.*—In the garden, flowering is continuous from spring until fall.

*Inflorescence size.*—Length: About 3.8 cm. Diameter: About 4.5 cm.

*Flower size.*—Diameter: About 1.6 cm. Tube length: About 2.3 cm. Tube diameter: About 2 mm.

*Flower color.*—Petal, upper surface: Between 88B and 88C. Petal, lower surface: Close to 85A. Throat: Between 85A and 86D; hairs, 86C.

*Calyx.*—Length: About 1.4 cm. Color: 144A.

*Reproductive organs.*—Not conspicuous; usually four stamens and one pistil; typical of Verbena. Seed production has not been observed.

Disease resistance: Under commercial conditions, resistance to pathogens common to Verbena has not been observed.

It is claimed:

1. A new and distinct cultivar of Verbena plant named 'Balwildaav', as illustrated and described.

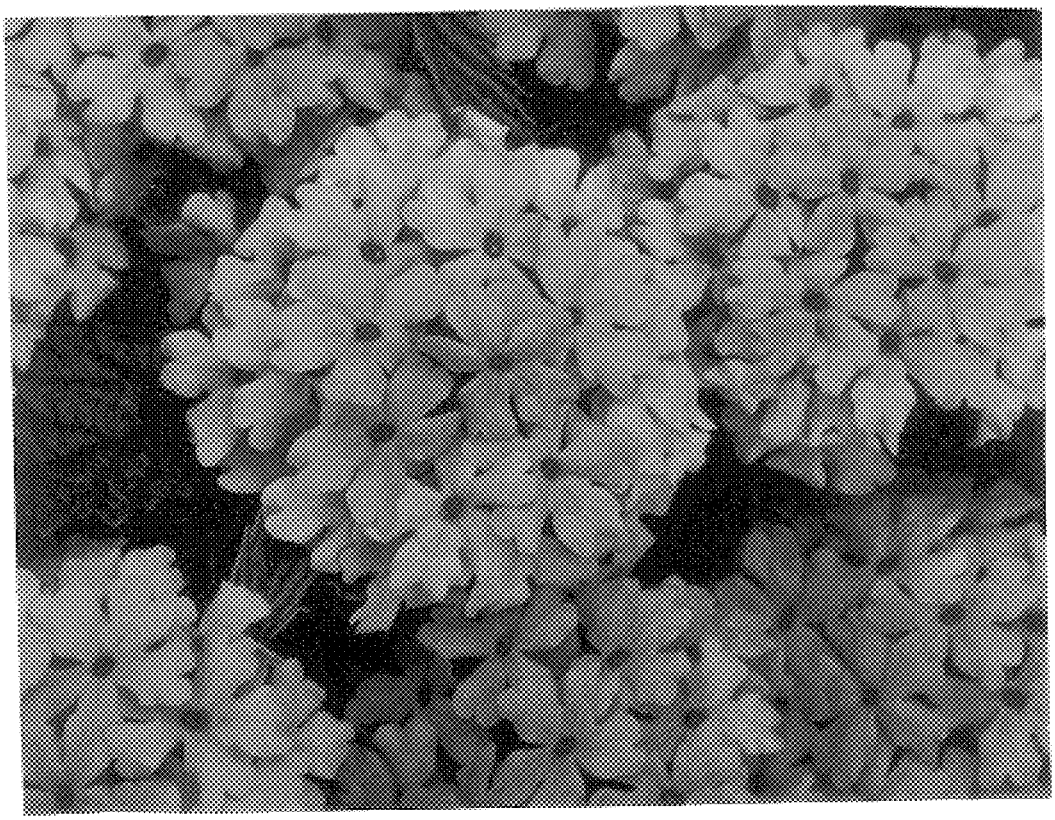

* * * * *